United States Patent [19]

Pinyan et al.

[11] Patent Number: 4,735,088

[45] Date of Patent: Apr. 5, 1988

[54] ATMOSPHERIC VARIABLE COMPENSATION METHOD AND SYSTEM FOR USE WITH AUTOMATED INSPECTION SYSTEMS

[75] Inventors: James A. Pinyan, Sunnyvale; B. Shawn Buckley, San Jose; Kenneth L. Blanchard, Milpitas, all of Calif.

[73] Assignee: Cochlea Corporation, San Jose, Calif.

[21] Appl. No.: 908,715

[22] Filed: Sep. 18, 1986

[51] Int. Cl.$^4$ .................. G01S 15/36; B07C 5/34
[52] U.S. Cl. .................. 73/629; 367/99; 367/902; 209/590
[58] Field of Search ........... 73/627, 628, 629, 571, 73/599, 620; 367/99, 902; 209/590

[56] References Cited

U.S. PATENT DOCUMENTS

| | | | |
|---|---|---|---|
| 3,438,493 | 4/1969 | Goble | 209/590 |
| 3,818,425 | 6/1974 | Peynaud et al. | 367/902 |
| 4,287,769 | 9/1981 | Buckley | 73/627 |
| 4,576,286 | 3/1986 | Buckley et al. | 367/902 |
| 4,581,726 | 4/1986 | Makino et al. | 367/99 |

*Primary Examiner*—John Chapman
*Attorney, Agent, or Firm*—Burns, Doane, Swecker & Mathis

[57] ABSTRACT

An acoustic inspection system includes acoustic transducers to transmit and receive continuous acoustic waves at a constant frequency. Changes in phase and/or amplitude of acoustic waves reflected at different times from a fixed reference target through an isothermal transmission medium are detected. The temperature of the acoustic transmission path is controlled in response to the detected phase changes to maintain the wavelength of acoustic waves constant independent of changes in humidity and barometric pressure.

16 Claims, 1 Drawing Sheet

ATMOSPHERIC VARIABLE COMPENSATION METHOD AND SYSTEM FOR USE WITH AUTOMATED INSPECTION SYSTEMS

BACKGROUND OF THE INVENTION

1. Field of the Invention

The present invention generally relates to automated inspection systems for identifying geometric characteristics of physical objects by transmission and reception of reflected sonic waves and, more particularly, to ways and means for compensating for atmospheric variables that affect operation of such systems.

2. State of the Art

In manufacturing assembly operations, including operations performed by robotic assembler machines, it is usually important that components are non-defective and are presented for assemblage in particular spatial orientations. These requirements arise because conventional assembler machines lack sufficient dexterity and machine intelligence to distinguish non-conforming parts from acceptable parts, or to handle objects that are not presented in certain prescribed positions. As a result, automated assembly systems often include custom-designed inspection and parts feeding systems whose cost may be several times the cost of the assembler machines. Also, inspection and feed systems often must be redesigned for new components that are to be automatically assembled. Thus, while robotic assembler machines may be repeatedly re-programmed with software to handle a variety of assembly tasks and parts, many conventional inspection and feed systems are not as versatile.

Numerous types of inspection devices have been designed to prevent misoriented, defective and otherwise non-conforming components from reaching assembly lines. At factories where components are manufactured, such inspection devices may be utilized to detect and help correct flaws resulting from manufacturing processes. At factories where components are assembled, such inspection devices may be utilized to detect conditions that cause defects in assembled products. These automated inspection devices often replace human inspectors, especially for inspection tasks which are difficult, tedious or expensive for humans to perform.

To improve the effectiveness and reduce the cost of automated inspection devices, attempts have been made to provide machines with the ability to remotely discern geometrical characteristics of objects—in essence, to "see" objects without physically touching them. (The phrase "geometrical characteristics" refers to external physical properties of objects and includes parameters such as position, orientation and shape.) To this end, some automated inspection systems have used optical equipment to sense changes in light reflected from objects. Although some optical systems have been successful, such systems often require extensive capabilities fo signal processing and computation.

Automated inspection systems of a somewhat different nature have been provided to recognize geometric characteristics of objects through transmission and reception of reflected waves in acoustic or electromagnetic fields that interact with inspected objects; the diffraction or scattering patterns of waves in the fields provide distinct "signatures" of the objects. In this regard, attention is drawn to U.S. Pat. Nos. 4,095,475; 4,200,921; 4,287,769; 4,479,241; 4,557,386 and 4,576,286 to Bruce S. Buckley. Such inspection systems, as compared to optical systems, usually require less capacity for signal processing and computation.

In one type of inspection system utilizing acoustic fields, measurement is made of time delays between sending and first receiving reflected sonic pulses. To completely determine shapes by such techniques, a transmitter and receiver must scan inspected objects, or multiple transmitters and receivers must be provided so that sound waves are reflected from various facets of inspected objects. In either case, facets of objects further from transmitters and receivers provide longer time delays than facets closer to transmitters and receivers. Measurement difficulties arise in such systems, however, because facets closer to transmitters and receivers than a facet of interest can mask measurement of the latter facet because pulses reflected from it are not "first received."

In another type of acoustic inspection system, continuous acoustic waves with a broad range of controllably-varied frequencies are used to establish fields about inspected objects, and measurements are made of the frequencies of reflected waves. In this technique, known as "continuous wave frequency modulation", electrical signals corresponding to reflected acoustic waves are provided by transducers and electronically translated into frequency domain signals, usually by Fourier transform algorithms. In such systems, geometrical characteristics can be determined by frequency modulation techniques because facets of objects further from transmitters and receivers provide responses at higher frequencies than facets closer to transmitters and receivers.

In still another type of acoustic inspection system, single-frequency continuous acoustic waves, usually sinusoidal, are directed towards objects presented for inspection. This technique is known as "phase-monitoring" because early systems measured only the phase of reflected waves; however, present systems provide both phase and amplitude information for reflected waves. According to phase-monitoring techniques, reflected waves have the same frequency as transmitted waves but differ from transmitted waves in amplitude and phase. An advantage of phase-monitoring techniques is that highly accurate digital and analog filters can be used; such filters, because they operate at a single frequency, are more easily constructed than the broadband filters required in frequency modulation techniques. Single-frequency phase-monitoring inspection systems are taught, for example, in U.S. Pat. Nos. 4,200,921 and 4,287,769. In phase-monitoring systems, geometrical characteristics of inspected objects can be determined because facets of objects further from receivers provide reflected waves having greater phase differences relative to emitted waves than facets closer to receivers. Because the acoustic signals are not pulsed in phase-monitoring systems, the systems avoid problems arising from close facets masking further facets and from multiple reflections as are encountered in other types of inspections systems utilizing acoustic fields In acoustic systems using phase-monitoring techniques, it is typical to provide one or more arrays of transmitting transducers to establish acoustic fields and, likewise, to provide one or more arrays of receiver transducers to detect distortions, or scattering, caused by inspected objects in the fields. Phase and amplitude information in th systems is compared, usually by a programmed computer, to corresponding information for objects that are known to be non-defective. Computer control is used to orchestrate the data gathering processes and to analyze amplitude and phase information. In some instances, pattern-recognition algorithms can be employed to reduce field information to a scalar quantity that indicates the extent of similarity of inspected objects to objects of known geometrical characteristics.

With respect to inspection systems that use acoustic techniques to detect geometrical characteristics of objects, it is known that temperature variations along transmission paths can affect acoustic measurements. Such temperature variations can occur in the atmosphere within the inspection system and in the acoustic transducers themselves. Thermal effects on measurements arise because the speed of sound generally increases with the temperature of materials defining the transmission path. For example, air temperature variations along an acoustic transmission path can cause substantial uncontrolled "drift" in acoustic signal measurements; normally, drift in wave properties must be minimized in acoustic systems to maintain inspection integrity and accuracy.

It is also known that automated acoustic inspection systems can employ statistical methods to process electrical signals derived from the acoustic waves. In such systems, inspected objects are deemed non-defective if waves reflected from the objects have characteristics that fall within predetermined statistical ranges, usually expressed in terms of standard deviations or variances. Also, acoustic inspection systems that employ statistical methods are especially adaptable for "learning" processes. Learning processes normally depend upon "teaching" a system by initially inspecting objects that are known to be acceptable and, then, deriving statistical measures for comparison purposes with objects of unknown configurations that are presented for inspection. The effectiveness of such learning processes depends upon the extent to which signals associated with acceptable objects have stable statistical deviations; if reference signals drift substantially, statistical ranges may change, measurements may become inexact, and frequent "relearning" may be necessary.

In the environment of a typical factory, temperature variations of several degrees can occur rapidly enough to substantially affect acoustic inspection systems. For example, factory temperatures can be rapidly changed by two or three degrees by opening exterior doors or windows, by operating HVAC (heating, ventilating and air-conditioning) equipment, or by operating machinery in the factory. To avoid signal drift in acoustic inspection equipment in such environments, the prior art teaches that temperatures along acoustic transmission paths and at transducers in acoustic inspection equipment should be held constant independent of ambient conditions. Typically, temperature control within inspection equipment is accomplished by heaters and thermostatic controls. Regardless of the accuracy of such controls, however, unexpected and undesired wavelength variations of substantial magnitude have been observed; the variations have been detected by repeated inspections of stationary objects, and have been found to be more severe in factory environments than in laboratories.

A method to compensate for the effects of temperature on acoustic signals in phase-monitoring systems is suggested in U.S. Pat. No. 4,287,769. As explained in the patent, acoustic phase-monitoring systems use acoustic wavelength as the standard unit for detecting dimensions of inspected objects, and accurate measurements become problematical when acoustic wavelengths vary due to changes in temperature. The patent also points out that acoustic wavelengths will change with humidity and with velocity of a transmission medium. According to the patent, compensation for changes in transmission medium properties can be made by open-loop controls. In one open-loop control technique, for example, temperature changes in the transmission medium are measured and, based upon the measurements, an algorithm is employed to alter the frequency of emitted acoustic waves to maintain constant acoustic wavelength. The suggested algorithm, which is applicable to many gaseous mediums, is:

$$f = \frac{1}{\lambda} [\gamma RT]^{\frac{1}{2}}$$

where f is the emitted frequency, $\lambda$ is the wavelength to be maintained constant, $\gamma$ is the ratio of specific heats for the medium, R is the universal gas constant, and T is temperature (absolute) of the transmission medium. In situations where frequency adjustments based upon the preceding algorithm did not completely compensate for temperature-related changes in the properties of the transmission medium, the lack of compensation was believed to be caused, for example, by errors in the assumed values of $\gamma$ and R, or errors in measuring temperature T, or by computation errors.

Regardless of the cause, however, uncontrolled wavelength changes in acoustic inspection systems of the phase-monitoring type can result in inspection errors. Such errors are usually categorized either as false acceptances or false rejections. A "false acceptance" is usually defined as an error arising from accepting objects which are defective; a "false rejection" error is usually defined as an error arising from rejecting objects which are not defective. False acceptance errors can severely affect automated assembly operations and thus can be quite costly and time consuming. False rejection errors, although often having less serious immediate consequences than false acceptance errors, nevertheless can cause problems if rejection rates for acceptable objects are high. Accordingly, efforts should be made to avoid both type of errors.

OBJECTS AND SUMMARY OF THE INVENTION

Generally speaking, an object and advantage of the present invention is to provide improvements in automated inspection systems that identify geometrical characteristics of objects in order to minimize the number of objects which are erroneously accepted by the inspection systems and, also, to minimize the number of acceptable objects which are erroneously rejected.

More specifically, an object and advantage of the present invention is to provide ways and means applicable to phase-monitoring types of acoustic inspection systems to compensate for changes in acoustic signal properties caused by exogenous atmospheric factors including temperature, humidity and atmospheric pressure.

In accordance with the preceding objects, the present invention provides an improved phase-monitoring type of acoustic inspection system comprising: an array of acoustic transducers to transmit and receive acoustic waves reflected from objects presented for inspection; means to detect changes in acoustic waves reflected at different times from a fixed target; means for heating the path of travel of the acoustic waves; and means to control the heating means in response to the detected changes so that the wavelength of acoustic waves is maintained substantially constant regardless of changes in atmospheric variables affecting the speed of sound along the acoustic transmission paths.

Further, the present invention provides a method for controlling phase-monitoring types of acoustic inspection systems comprising the steps of: at different time periods, detecting changes in acoustic waves reflected from a fixed target; heating at least a portion of the acoustic travel path to a set-point temperature; and adjusting the set-point temperature to minimize changes in wavelength of the reflected acoustic signals caused by atmospheric variations.

Further objects and advantages of the present invention may be ascertained by those skilled in the art from the following description and appended drawings, which are offered by way of example of the preferred embodiment of the present invention.

DETAILED DESCRIPTION OF THE PREFERRED EMBODIMENT

Figure 1:
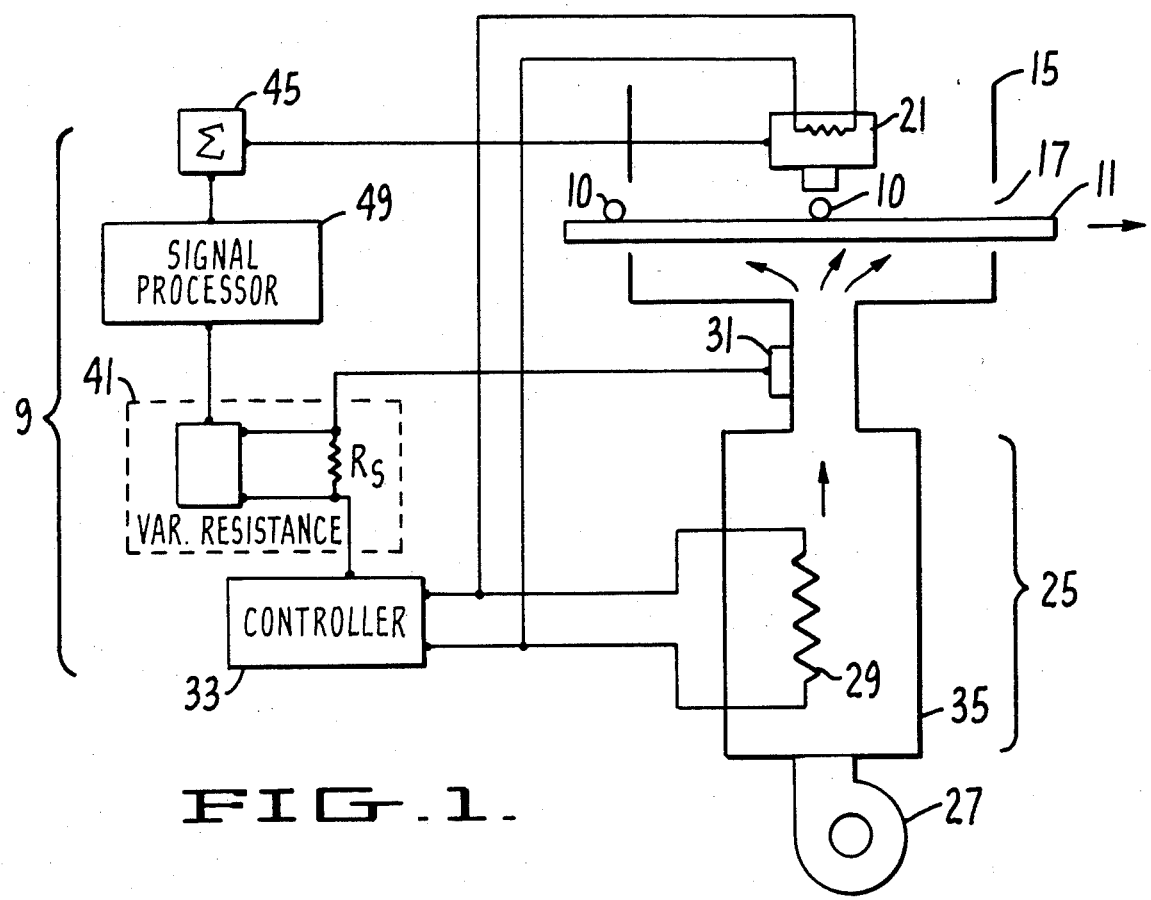
FIG. 1 is a functional diagram of an automated inspection system incorporating an atmospheric variable compensation system according to the present invention.

FIG. 1 generally shows an automated system 9 for identifying external geometrical characteristics of objects 10 by phase-monitoring techniques that depend upon transmission and reception of reflected sonic waves that are continuous at a single frequency or a narrow band of frequencies. Objects 10 presented for inspection are carried through system 9 on conveyor 11 which, in practice, may have various configurations. For example, conveyor 11 can be an inclined chute or a moving belt that carries objects through inspection system 9 at constant velocity or that causes objects to pause momentarily at a predetermined location within inspection system 9. Further, conveyor 11 can include devices to move objects to a common orientation for inspection.

Still speaking generally of FIG. 1, inspection system 9 includes a closed housing 15 having ports 17 to accommodate travel of objects 10 into, and out of, the housing on conveyor 11. Within housing 15, an array 21 of acoustic transducers is stationarily mounted to establish an acoustic field about objects 10 and to detect phase and amplitude differences in wave reflected from the objects. Transducer array 21 and the general operation of a detection system utilizing such transducers can be, for example, as taught in U.S. Pat. Nos. 4,095,475, 4,200,921 and 4,557,386. In such systems, phase and amplitude information provided by transducer array 21 is processed to provide inspection and positioning information. The frequency of acoustic waves provided by the transducer array 21 is normally in the range from about 20 to about 200 KHz.

According to the present invention, atmospheric parameters within housing 15 are controlled independent of the environment outside the housing. The external, or ambient, environment can be described in terms of barometric pressure, temperature, and humidity. It should be noted that any one of those variables can change independently; for example, humidity may increase without changes in temperature or barometric pressure. Also, two or more of the atmospheric variables may change simultaneously, either in the same or in opposite directions; for example, humidity may increase at the same time that temperature decreases. Most importantly, changes in any of these atmospheric variables can alter the velocity of sound within housing 15 by changing the density of the mediums along the sonic transmission paths and, therefore, can affect operation of inspection system 9.

In the illustrated embodiment of system 9, atmospheric variables within housing 15 are controlled by a conditioning system generally indicated by the bracket 25. Specifically, conditioning system 25 includes an air blower 27, an electrical heater 29, and an associated sensor 31, temperature controller 33 and a variable resistance 41. Blower 27 is arranged to force air through a duct 35 into housing 15, and electrical heater 29 is mounted in duct 35 to heat the forced air in a controlled manner. The specific design of blower 27 and heater 29 is a matter of choice, and various suitable devices are commercially available. In practice, temperature sensor 31 is a thermistor which is stationarily mounted at some convenient location near transducer array 21 in the path of the heated air and is connected in electrical series in a circuit including temperature controller 33 and variable resistance device 41. The thermistor provides electrical resistance in the circuit proportional to the temperature of the air surrounding sensor array 21. (Although thermistors can have negative temperature coefficients, it will be assumed for purposes of the following description that thermistor resistance increases with increasing temperatures.) Heater 29 is connected to temperature controller 33 in a conventional manner so that its output energy is determine by the controller.

Operation of conditioning system 25 will now be described, but without reference to variable resistance device 41. Excluding that device, conditioning system 25 includes blower 27, electrical heater 29, temperature sensor 31 and temperature controller 33. In normal operation, the energy output of heater 29 is thermostatically controlled by controller 33 to keep the temperature at temperature sensor 31 constant, usually substantially above ambient. Thus, the energy output of heater 29 increases when temperatures within housing 15 fall below a preselected temperature, usually called the "set-point" temperature, and the energy output of heater 29 decreases when temperatures within housing 15 exceed the set-point temperature. In practice, temperature variations adjacent transducer array 21 can usually be controlled to less than about ±1° F.

Further with regard to inspection system 9 in FIG. 1, there will now be described a subsystem which modifies the above-described operation of conditioning system 25 in order to minimize changes in wavelength of acoustic waves along transmission paths within housing 15. Generally speaking, the subsystem includes a detector 45 connected to at least one pair of transmitter and receiver transducers in array 21 to detect signal phase shifts or amplitude changes, or both, sensed by the transducers in array 21. The subsystem further includes a signal processor 49 connected to receive signals from detector 45 and to provide control signals to variable resistance device 41 connected to processor 49. In practice, signal processor 49 is a microprocessor or a similar computational device and is programmed to include algorithmic relationships such as will be described in conjunction with FIGS. 2–4.

Figure 2:
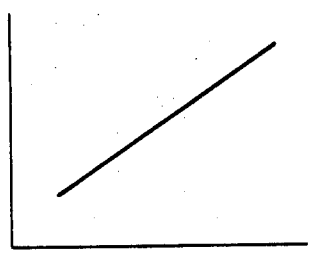
FIG. 2 is a graphical representation of a relationship between FIT and temperature in the system of FIG. 1.

FIG. 2 generally shows an empirical relationship between a variable "FIT" and temperature as sensed by sensor 31 in housing 15 under conditions of constant pressure (i.e., isobaric conditions) and constant humidity in housing 15. In other words, FIG. 2 shows the relationship between FIT-described phase changes for reflected acoustic waves in system 9 where temperature within housing 15 is the only atmospheric variable allowed to independently change. In practice, FIT is a scalar number that represents phase and amplitude information relating to the acoustic field established in housing 15; it is derived from the output of transducer array 21 as processed by signal processor 49. Because phase measurements in system 9 depend upon the position of transducer array 21, the value of FIT under steady-state conditions will vary from system to system; in general, however, the value of FIT can be understood to be a weighted average of phase and amplitude information detected by transducer array 21. For purposes of simplifying the following description, however, it can be assumed that FIT represents only phase information as measured in radians; further explanation of FIT is provided in U.S. Pat. No. 4,557,386. The relationship between FIT and temperature will be generally linear, as indicated by FIG. 2, when atmospheric variables such as humidity and pressure are constant within the system. In an operating environment, the value of FIT provided by inspection system 9 will depend upon the external geometric characteristics of objects presented for inspection; however, the values of FIT shown in FIG. 2, are to be understood to be based upon reflections from a target that has constant geometrical characteristics and which is inspected at different times and at different temperature conditions with other atmospheric variables unchanged. The fixed target may be any stationary reference object within housing 15 having geometric characteristics that do not vary substantially with time or atmospheric variables.

Figure 3:
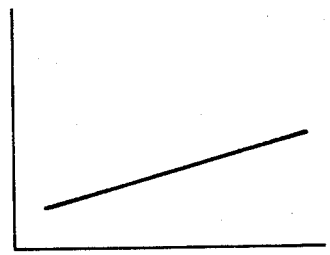
FIG. 3 is a graphical representation of a relationship between FIT and humidity within the syste of FIG. 1.

FIG. 3 shows an empirical relationship between FIT and absolute humidity in housing 15 under isothermal and isobaric conditions. (Humidity can be expressed in units of kilograms of $H_2O$ per kilogram of air.) In practice, the graph of FIG. 3 is determined by operating inspection system 9 with gaseous atmospheres in housing 15 having different humidities but constant temperature and pressure. Here again, the values of FIT are based upon reflections from a target that has constant geometrical characteristics. The range of humidities in FIG. 3 is about 0% to about 20%, and the range of the FIT values is about 0 to about 150 milli-radians. The linear relationship depicted in FIG. 3 is a fitted curve.

Figure 4:
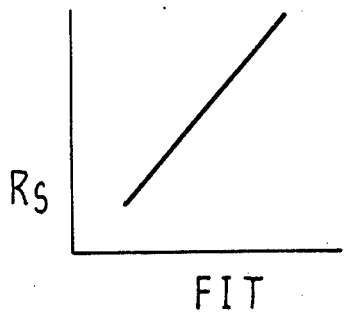
FIG. 4 is a graphical representation of a relationship between FIT and resistance of an element of the temperature control system in FIG. 1.

FIG. 4 shows an empirical relationship between FIT and the resistance value $R_S$ of variable resistance 41. The graph of FIG. 4 is determined by operating inspection system 9 with constant humidity and pressure while varying the values of resistance $R_S$. Although the linear relationship shown in FIG. 3 is a fitted curve, actual relationship are substantially linear over reasonable ranges. The effects of changing resistance values $R_S$ on conditioning system 25 can be best explained by reference to FIG. 5.

Figure 5:
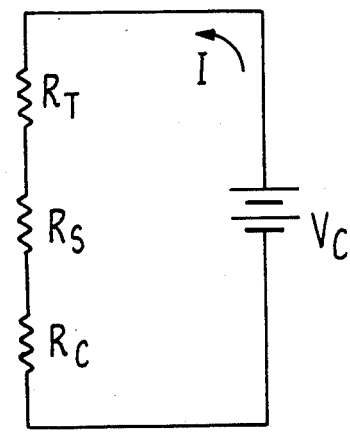
FIG. 5 is a simplified schematic diagram to illustrate operation of a temperature control system in the system of FIG. 1.

FIG. 5 shows a series circuit for controlling the temperature within housing 15. The circuit includes a constant voltage source ($V_c$), the resistance of temperature sensor 31 ($R_T$), the resistance of variable resistance 41 ($R_S$), and the resistance of temperature controller 33 ($R_C$). The current flowing in the circuit will depend upon the values of resistances $R_T$, $R_S$, and $R_C$ in accordance with Ohm's law; accordingly, the voltage across resistor $R_C$ will decrease with increasing values of resistances $R_T$ or $R_S$ and, conversely, will increase with decreasing values of resistances $R_T$ and $R_S$.

Thus it can be understood that the graph in FIG. 4 is derived by selectively varying resistance RS and observing the resultant changes in FIT values caused by changes in the thermostatically-controlled temperature in housing 15 with humidity and pressure held constant. The temperature range for the graph of FIG. 4 is typically about three to four degrees Fahrenheit.

Operation of the complete system of FIG. 1 will now be described. Under conditions where there are no changes in pressure or humidity, temperature sensor 31 and temperature controller 33 in conditioning system 25 cooperatively operate to maintain the atmosphere within housing 15 at, or near, a preselected constant set-point temperature determined by the series resistances of temperature sensor 31, variable resistor 41, and temperature controller 33. During such operation, temperature controller 33 operates as a conventional thermostat to control heater 29 according to the voltage which appears across resistor $R_C$; accordingly, energy output from heater 29 increases if the voltage across resistor $R_C$ increases and, conversely, energy output from heater 29 decreases if the voltage across resistor $R_C$ decreases. During such times, changes in voltage across resistor $R_C$ are caused by changes in the resistance $R_T$ due to temperature effects; for example, an increase in temperature will decrease resistance $R_T$ and will, in turn, cause an increase in voltage across resistance $R_C$.

While conditioning system 25 is operating as described above, sonic waves are generated and received by transducers within array 21. The sensor transducers convert reflected acoustic wave energy to electrical signals that can be processed and analyzed to provide amplitude and phase information. The processing and analyzing elements (not shown) may include devices such as multiplexors, analog amplifiers and filters, digital filters, and microprocessors.

Also during operation of the system of FIG. 1, one or more of the acoustic transducers in array 21 are utilized to monitor changes in FIT as related to changes in phase or amplitude, or both, of waves reflected from a selected fixed target. If there are no changes in FIT at different times for the signals reflected from the fixed target, a conclusion can be drawn that acoustic properties within housing 15 have not changed; the result of this conclusion, in terms of system control, is that temperature within the housing is held constant at the then-current value. However, if FIT changes between two time periods during which the temperature within housing 15 is constant, the conclusion can be drawn that the changes are due to atmospheric parameters other than temperature; for example, the changes in FIT may be due to isothermal increases in humidity or pressure of the atmosphere within housing 15.

In the event that changes in FIT are detected by detector 45 under isothermal conditions, signal processor 49 operates to cause a change in the value of resistance $R_S$ within variable resistor device 35. Specifically, resistance $R_S$ is increased if phase-shift detector 45 indicates that the FIT values have increased isothermally; conversely, resistance $R_S$ is adjustably decreased if FIT values have decreased isothermally. The effect of changing resistance $R_S$ is to change the set-point temperature for conditioning system 25. Specifically, an increase in the value of resistance $R_S$ will cause conditioning system 25 to increase temperatures in housing 15 and, conversely, a decrease in the value of resistance $R_S$ will cause conditioning system 25 to decrease temperatures in housing 15. Thus, after a change in resistance $R_S$, temperature controller 33 operates to bring the atmosphere within housing 25 to a new steady-state temperature. The temperature sought by conditioning system 25 and the controlled change in resistance $R_S$ are predetermined according to the empirically-derived relationship between FIT and temperature as shown in FIG. 2 for the system, with the object of changing temperature sufficiently to maintain FIT values constant in the system.

Thus, the system of FIG. 1 is controlled to change temperatures within housing 15 in response to changes in atmospheric factors. Operation of the system of FIG. 1 is therefore, substantially different from systems wherein temperatures are maintained constant at all times. Further, the system of FIG. 1 employs closed-loop control with the feedback signals being FIT values for waves reflected from a reference target. In practice, the system can often provide more than an order of magnitude improvement in resolution.

With the preceding description in mind, it can be understood that the temperature of transducer array 21 can be controllably varied as well as the temperature of the atmosphere within housing 15. In systems where transducer array 21 comprises a substantial portion of the acoustic transmission path, control of its temperature will serve substantially the same purpose as changing the atmospheric temperature within housing 15. Also, controls can be provided to controllably change both the temperature of the atmosphere within housing 15 and the temperature of transducer array 21.

As another alternative, the transmission frequency of acoustic waves under isothermal conditions within housing 15 can be controlled to alter the wavelength of sound within the housing. Thus, controlled changes in transmission frequency can be used to correct for changes in FIT due to variations in humidity or barometric pressure. According to this alternative, an empirical relationship is found between values of FIT and transmission frequency under isothermal and isobaric conditions. Once that relationship is determined, signal processor 49 is programmed to vary the frequency of acoustic waves transmitted from transducer array 21 in accordance with detected changes in FIT. Such a system would normally operate under isothermal conditions as previously described, and one or more transducers in array 21 would be utilized to monitor changes in FIT for waves reflected from the fixed target; then, upon occurrence of changes in FIT under isothermal conditions, the transmission frequency of transducer array 21 would be controllably varied to maintain acoustic wavelength constant and, hence, to cancel the detected change in FIT.

Although the present invention has been described with particular reference to the illustrated embodiments, such disclosure should not be interpreted as limiting. Various alterations and modifications will no doubt become apparent to those skilled in the art after having read the preceding disclosure. For example, workers skilled in the art of control systems can readily appreciate that integral or differential action can be readily added to the system of FIG. 1 by software programming of signal processor 49. The integral action would provide smoother operation of the system of FIG. 1, and differential action would enhance the ability of the system to respond to rapidly changing environmental conditions. With either differential or integral action, however, the basic functioning of system 9 would not change. In view of these alternatives and others, it is intended that the appended claims be interpreted as covering all alternative embodiments and equivalents as fall within the spirit and scope of the present invention.

We claim:

1. An inspection system for identifying changes in geometrical characteristics of objects by phase-monitoring techniques for detecting changes in at least one of phase and amplitude in fields of continuous acoustic waves of constant wave length reflected from objects presented for inspection comprising:

- acoustic transducer means to transmit and receive acoustic waves reflected from objects presented for inspection;
- detection means to detect at least one of phase and amplitude changes in acoustic waves transmitted at a single frequency and reflected at different times from a target that has non-varying geometrical characteristics;
- heating menas for controllably heating at least a portion of the path of travel of said acoustic waves;
- control means to control the heating means in response to change detected by the detection means to maintain the wavelength of acoustic waves constant regardless of changes in atmospheric variables affecting the speed of sound in the inspection system.

2. An inspection system as defined in claim 1 wherein the control means further include temperature sensor means and temperature controller means connected to the heating means to provide thermostatic control of temperature within the inspection system.

3. An inspection system as defined in claim 2 wherein the temperature controller means provides thermostatic control about a set-point temperature.

4. An inspection system as defined in claim 3 wherein the control means further includes means to vary the set point of the temperature controller in response to changes detected by the detection means.

5. An inspection system as defined in claim 4 wherein the control means includes a microprocessor programmed with a relationship between the phase or amplitude, or both, of reflected waves and set point values, that determines set point values which are necessary to maintain constant acoustic wavelengths in the inspection system.

6. An inspection system for identifying geometrical characteristics of objects by phase-monitoring techniques for detecting changes in at least one of phase and amplitude in a field of continuous acoustic waves of generally constant wavelemgth reflected from objects presented for inspection, comprising:
- acoustic transducer means to transmit and receive acoustic waves reflected from objects presented for inspection;
- detection means to detect changes in at least one of phase and amplitude of acoustic waves reflected at different times from a target that has non-varying geometrical characteristics;
- heating means for heating at least a portion of the transmission path of said acoustic waves; and
- control means to control the heating means to change the temperature of at least a portion of said transmission path in response to said changes detected by the detection means, thereby to maintain the wavelength of acoustic waves constant following changes in atmospheric variables affecting the speed of sound in the inspection system under isothermal conditions.

7. An inspection system as defined in claim 6 wherein the control means further include temperature sensor means, temperature controller means connected to the heating means to provide thermostatic control of temperature within the inspection system in response to the temperature sensor means, and variable resistor means to define the set point of said temperature controller means.

8. An inspection system as defined in claim 7 wherein the control means controls the variable resistor to vary the set point of the temperature controller means in response to said changes detected by the detection means.

9. An inspection system as defined in claim 8 wherein the control means is programmed with a relationship between the phase or amplitude, or both, of reflected waves and set point values, and the control means employs said relationship to control said variable resistor to change the temperature of the acoustic transmission path sufficiently to maintain constant acoustic wavelengths along the path.

10. An inspection system as defined in claim 9 wherein the heating means is connected to heat air through which the acoustic waves travel during inspection of objects.

11. In inspection system as defined in claim 10 wherein the heaing means is connected to heat the acoustic transducer means.

12. In an acoustic sensing system for identifying geometrical characteristics of objects including acoustic transmitters for transmitting continuous acoustic waves of generally constant frequency that interact with objects in a sensing region, acoustic receivers for detecting reflected acoustic waves, means for processing electrical signals from said acoustic receivers to obtain amplitude and phase information that yields parameters indicative of geometric characteristics of inspected objects, the improvement comprising:
- detection means to detect changes in at least one of phase and amplitude of acoustic waves reflected under isothermal conditions from a target that has substantially non-varying geometrical characteristics;
- heating means or heating at least a portion of the path of travel of said acoustic waves to a selected setpoint temperature;
- control means to control the heating means to change said selected setpoint temperature in response to changes detected by the detection means, thereby to maintain the wavelength of acoustic waves constant regardless of changes in atmospheric variables.

13. A method for controlling an automated acoustic inspection system of the type wherein geometrical characteristics of objects are identified by establishing a field of continuous acoustic waves of substantially constant frequency about objects presented for inspection and changes in waves reflected from the objects are detected under isothermal conditions, comprising the steps of:
- at different time periods, detecting changes in acoustic waves reflected from a reference target that has constant geometrical characteristics;
- heating at least a portion of the acoustic travel path to a selected temperature above ambient;
- adjusting said selected temperature of the heated portion of the transmission path in response to said detected changes to minimize changes in the wavelength of the acoustic waves caused by atmospheric variables.

14. A method as defined in claim 13 including thermostatically controlling said selected temperature about a selected set point temperature.

15. A method as defined in claim 14 including the step of varying the selected set point temperature in response to said detected changes.

16. A method as defined in claim 15 including the step of providing an algorithm to define the relationship between phase changes and set point values under conditions of constant humidity and barometric pressure.

* * * * *